US008580306B2

(12) United States Patent
Staniforth et al.

(10) Patent No.: US 8,580,306 B2
(45) Date of Patent: *Nov. 12, 2013

(54) PARTICLES FOR USE IN A PHARMACEUTICAL COMPOSITION

(75) Inventors: John Nicholas Staniforth, Bath (GB); David Alexander Vodden Morton, Bath (GB)

(73) Assignee: Vectura Limited, Chippenham (GB)

(*) Notice: Subject to any disclaimer, the term of this patent is extended or adjusted under 35 U.S.C. 154(b) by 0 days.

This patent is subject to a terminal disclaimer.

(21) Appl. No.: 10/433,135

(22) PCT Filed: Nov. 30, 2001

(86) PCT No.: PCT/GB01/05305
§ 371 (c)(1),
(2), (4) Date: Nov. 28, 2003

(87) PCT Pub. No.: WO02/43700
PCT Pub. Date: Jun. 6, 2002

(65) Prior Publication Data
US 2004/0071635 A1    Apr. 15, 2004

(30) Foreign Application Priority Data

Nov. 30, 2000 (GB) .................................. 0029261.5
Dec. 19, 2000 (GB) .................................. 0030946.8
Oct. 5, 2001 (GB) .................................. 0124009.2

(51) Int. Cl.
*A61K 9/00* (2006.01)
*A61K 9/14* (2006.01)

(52) U.S. Cl.
USPC .......................................... 424/489; 424/46

(58) Field of Classification Search
USPC .................................................. 424/46, 489
See application file for complete search history.

(56) References Cited

U.S. PATENT DOCUMENTS

| | | | | |
|---|---|---|---|---|
| 4,906,476 | A | 3/1990 | Radhakrishnan | 424/450 |
| 5,188,837 | A | 2/1993 | Domb | 424/450 |
| 5,192,528 | A | 3/1993 | Radhakrishnan | 424/45 |
| 5,320,906 | A * | 6/1994 | Eley et al. | 428/402.2 |
| 5,413,804 | A * | 5/1995 | Rhodes | 426/583 |
| 5,506,203 | A | 4/1996 | Bäckström et al. | 514/4 |
| 5,518,187 | A * | 5/1996 | Bruno et al. | 241/5 |
| 5,612,053 | A | 3/1997 | Baichwal et al. | 424/440 |
| 5,655,523 | A | 8/1997 | Hodson et al. | 128/203.15 |
| 5,663,198 | A | 9/1997 | Reul et al. | 514/471 |
| 5,711,934 | A * | 1/1998 | Adjei et al. | 424/45 |
| 5,738,865 | A | 4/1998 | Baichwal et al. | 424/440 |
| 5,908,639 | A * | 6/1999 | Simpkin et al. | 424/489 |
| 5,931,809 | A | 8/1999 | Gruber et al. | 604/512 |
| 5,935,555 | A | 8/1999 | Stutts et al. | 424/45 |
| 5,993,846 | A * | 11/1999 | Friedman et al. | 424/434 |
| 5,997,848 | A * | 12/1999 | Patton et al. | 424/46 |
| 6,103,271 | A | 8/2000 | Morrison et al. | 424/490 |
| 6,153,224 | A * | 11/2000 | Staniforth | 424/490 |
| 6,178,414 | B1 | 1/2001 | Beckman et al. | 707/3 |
| 6,197,369 | B1 | 3/2001 | Watano et al. | 427/213 |
| 6,404,772 | B1 | 6/2002 | Beach et al. | 370/338 |
| 6,475,523 | B1 | 11/2002 | Staniforth | 424/70.1 |
| 6,477,670 | B1 | 11/2002 | Ahmadvand | 714/712 |
| 2003/0162835 | A1 | 8/2003 | Staniforth et al. | 424/46 |
| 2003/0165436 | A1 | 9/2003 | Staniforth et al. | 424/45 |
| 2003/0175214 | A1 | 9/2003 | Staniforth et al. | 424/45 |
| 2003/0185764 | A1 | 10/2003 | Staniforth et al. | 424/45 |
| 2004/0037785 | A1 | 2/2004 | Staniforth et al. | 424/46 |
| 2004/0047810 | A1 | 3/2004 | Staniforth et al. | 424/46 |
| 2004/0202616 | A1 * | 10/2004 | Keller et al. | 424/46 |
| 2005/0152849 | A1 | 7/2005 | Staniforth | 424/489 |
| 2006/0257491 | A1 | 11/2006 | Morton | 424/46 |

FOREIGN PATENT DOCUMENTS

| | | | |
|---|---|---|---|
| EP | 1430887 | 6/2004 | ............... A61K 9/00 |
| WO | WO 92/08447 | 5/1992 | |
| WO | WO 95/00127 | 1/1995 | |
| WO | 9619197 | 6/1996 | ............... A61K 9/12 |
| WO | 9619198 | 6/1996 | ............... A61K 9/12 |
| WO | WO 96/23485 | 8/1996 | |
| WO | WO 97/03649 | 2/1997 | |
| WO | WO 99/27920 | * 6/1999 | |
| WO | 9938493 | 8/1999 | ............... A61K 9/00 |
| WO | 0028969 | 5/2000 | ............... A61K 9/00 |
| WO | WO 00/27363 | * 5/2000 | |
| WO | WO 00/33811 | 6/2000 | |
| WO | WO 00/61108 | 10/2000 | |
| WO | 0230394 | 4/2002 | |

OTHER PUBLICATIONS

Nato et al. The Iron Steel Institute of Japan International, 1993, 33(9), pp. 915-924.*
Pharmaceutical Dosage Forms, Lieberman, H. A. and Lachman, L., Eds., Marcel Dekker, Inc.: New York, 1981, pp. 77-85.*
International Search Report of International Application No. PCT/GB01/05305 (5 pages).
"Preparation for Inhalation: Aerodynamic Assessment of Fine Particles—Fine Particle Dose and Particle Size Distribution"; European Pharmacopeia (supplement 2000); Sec. 2.9.18.
William C. Hinds; "Aerosol Technology, Properties, Behavior and Measurement of Airborne Particles; Second edition"; John Wiley & Sons, Inc.; pp. 51-52 and 402-408.
G. W. Hallworth et al., "The Twin Impinger: a Simple Device for Assessing the Delivery of Drugs from Metered Dose Pressurized Aerosol Inhalers"; J. Pharm. Pharmacol., vol. 39 (1987); pp. 988-972.
I. Colbeck; "Physical and Chemical Properties of Aerosols"; Blackie Academic & Professional; pp. 18-20.
Hamada, K. "The Surface Modification of Solid Particle by Adhesion of Liquid Using Hybridizer," Funtai Kagaku Kaishi, 1998, 35 (6), pp. 447-450 (English Abstract only).
Merriam-Webster Incorporated: Springfield, Massachusetts, 1993, pp. 311.

(Continued)

*Primary Examiner* — James H Alstrum Acevedo
(74) *Attorney, Agent, or Firm* — Maryellen Feehery Hank; Reed Smith LLP (57) ABSTRACT

The invention provides a method of making a composition for inhalation which includes the step of mixing particles of additive material having a diameter of not more than 2 μm with active particles, wherein the additive material is suitable for promoting the dispersal of active particles upon aerolization of a dry powder in a dry powder inhaler.

19 Claims, 6 Drawing Sheets

(56) References Cited

OTHER PUBLICATIONS

Abstract only of JP 05301810 Published Nov. 16, 1993.

Rotthäuser, Barbel, et al., "Optimization of an effervescent tablet formulation containing spray dried L-leucine and polyethylene 6000 as lubricants using a central composite design", European Journal of Pharmaceuticals and Biopharmaceutics, vol. 46, Issue 1, Jul. 1998, pp. 85-94.

Müller, Rainer H. and Peters, Katrin, "Nanosuspensions for the formulation of poorly soluble drugs I. Preparation by a size-reduction technique", International Journal of Pharmaceutics, 160(2) (1998), pp. 229-237.

Kawashima, Yoshiaki, et al., "Design of inhalation dry powder of pranlukast hydrate to improve dispersibility by the surface modification with light anhydrous silicic acid (AEROSIL 200)", International Journal of Pharmaceutics, 173 (1998), pp. 243-251.

Pillai, R.S. et al., "Controlled release from condensation coated respirable aerosol particles", J. Aerosol Sci (1994) vol. 25, No. 3, pp. 461-477.

Pharmaceutical powder compaction technology, Ed. Goran Alderborn and Christer Nystrom, Marcel Dekker, Inc, 1996, pp. 292-299.

Pharmaceuticals—The science of dosage form design, 2nd Edition, Ed. M.E. Aulton, Churchill Livingston, 2002, pp. 191-193.

Zeng, X.M. et al "Particle interactions in dry powder formulations for inhalation", Taylor & Francis, 2001, pp. 165-167.

Answer to Opposition to European Patent No. 1337239 by AstraZeneca AB and Norton Healthcare Limited dated Mar. 4, 2011.

Statement of Opposition by Norton Healthcare Ltd dated Jul. 21, 2010.

Statement of Opposition by AstraZeneca AB against European Patent No. 1337239 received at the European Patent Office on Jul. 21, 2010.

* cited by examiner

PARTICLES FOR USE IN A PHARMACEUTICAL COMPOSITION

The invention relates to pharmaceutical compositions for inhalation and to particles for use in such compositions.

Pulmonary administration is known for the delivery of drugs for the treatment of respiratory conditions such as asthma and is receiving increasing attention as a route for the delivery of systemic drugs such as insulin. Known devices for the administration of drugs to the respiratory system include pressurised metered dose inhalers (pMDI's) and dry powder inhalers (DPI's).

In pulmonary administration, the size of the active particles is of great importance in determining the site of the absorption. In order that the particles be carried deep into the lungs, the particles must be very fine, for example having a mass median aerodynamic diameter of less than 10 μm. Particles having aerodynamic diameters greater than 10 μm are likely to impact the walls of the throat and generally do not reach the lung. Particles having aerodynamic diameters in the range of 5 μm to 0.5 μm will generally be deposited in the respiratory bronchioles whereas smaller particles having aerodynamic diameters in the range of 2 to 0.05 μm are likely to be deposited in the alveoli.

Small particles are, however, thermodynamically unstable due to their high surface area to volume ratio, which provides significant excess surface free energy and encourages particles to agglomerate. In a dry powder inhaler, agglomeration of small particles and adherence of particles to the walls of the inhaler are problems that result in the active particles leaving the inhaler as large stable agglomerates or being unable to leave the inhaler and remaining adhered to the interior of the inhaler.

The uncertainty as to the extent of formation of stable agglomerates of the particles between each actuation of the inhaler and also between different inhalers and different batches of particles leads to poor dose reproducibility.

The increased efficiency of redispersion of the fine active particles from the agglomerates or from the surfaces of carrier particles during inhalation is regarded as a critical step in improving the efficiency of the dry powder inhalers.

In an attempt to improve the flow of the powder, dry powders for use in dry powder inhalers often include particles of an excipient material mixed with the fine particles of active material. Such particles of excipient material may be coarse, for example having a mass median aerodynamic diameter greater than 90 μm, (such coarse particles are referred to as carrier particles) or they may be fine.

WO96/23485 describes the addition of an additive material to a powder for inhalation including carrier particles and active particles to improve the respirable fraction of the active material. A preferred additive material is leucine.

WO97/03649 also describes the addition of leucine to powder compositions for dry powder inhalers, in which the compositions do not include carrier particles.

While the addition of the additive material to the compositions described in WO96/23485 and WO97/03649 gives improved respirable fractions of the active components, it would be desirable to make the effect of the additive material still more beneficial.

Propellant-based formulations for use with pressurised metered dose inhalers are also known and are widely used.

It has also long been desired to develop pharmaceutical formulations in which the pharmaceutically active substance is released over a comparatively long period of time in order to maintain the concentration of the active substance in the blood at a desired level for a comparatively longer period of time. An associated benefit is an increase in patient compliance with the dosing regime brought about by reducing the number of, and/or the frequency of, the administrations necessary to maintain the concentration of the active substance in the blood at the desired level.

Delayed release compositions have been developed for delivery of drug to the gastrointestinal tract and some such compositions are commercially available. Systems for the controlled delivery of an active substance through the skin have also been developed.

There remains a need to develop a delayed release composition for pulmonary administration having satisfactory properties.

The present invention provides a method of making a composition for inhalation which includes the step of mixing particles of additive material having a diameter of not more than 2 μm with active particles, wherein the additive material is suitable for promoting the dispersal of particles upon aerolisation of a dry powder in a dry powder inhaler.

Compositions for inhalation comprising the particles of additive material according to the invention may demonstrate improved dispersal of the active particles on actuation of the inhaler and/or delayed release of the active substance after deposition in the lungs. It is believed that those improved properties are achieved because the additive particles are smaller than known additive particles and can therefore more effectively surround or coat the active particles.

The term "particles of additive material" and the term "additive particles" are used interchangeably herein and refer to particles comprising or consisting of one or more additive materials. Preferably, the additive particles consist essentially of one or more additive materials. Where a large number of the particles of additive material are collected together, as will usually be the case in their manufacture, and the particles are dry, they will generally form a powder. The additive particles (before being mixed with other components to form a composition for inhalation) are preferably in the form of a powder.

Preferably, where the additive material is intended for use in a dry powder composition for a dry powder inhaler, it is not a sticky material at room temperature because sticky substances will tend to reduce the dispersability of the powder. Preferably, the additive material is a free flowing solid at room temperature.

Preferably, the particles of additive material have a diameter of not more than 1.5 μm, advantageously not more than 1 μm and most advantageously not more than 0.8 μm.

A variety of differently defined diameters are known to those skilled in the art of inhaler aerosols. As used herein, unless the context demands otherwise, the word "diameter" may refer to any one of the following known definitions of diameter.

i) Mass Median Aerodynamic Diameter (MMAD). The MMAD of particles of additive material of the present invention is determined using Multi-Stage Liquid Impinger in accordance with the method described in European Pharmacopoeia (supplement 2000) 2.9.18. (Aerodynamic assessment of fine particles) for powder inhalers.

ii) Volume Equivalent Diameter (VED). The VED is the diameter of a sphere having the same volume as that of the particle of additive material. The VED and methods of measuring the VED are discussed in Aerosol Technology, Properties, Behaviour and Measurement of Airborne Particles, Second Edition, William C. Hinds, Wiley-Interscience, John Wiley & Sons (see especially pages 51 and 52 and 402 to 408). For the purposes of the invention, the particles of additive material are regarded as having a VED of not more than a specified length, for example 2 μm, if 90% (by number) of those particles have a VED of less than that specified length.

iii) Volume median diameter (VMD). Volume median diameters can be measured by laser light scattering, for example, using a Malvern laser light scattering instrument.

iv) Stokes Diameter. The Stokes diameter is the diameter of the sphere which has the same density (density of the bulk material) and the same falling velocity as the particle of additive material. The Stokes diameter is discussed in Physical and Chemical Properties of Aerosols, Ed. I. Colbeck, Blackie Academic and Professional, Chapman & Hall. For the purposes of the invention, the particles of additive material are regarded as having a Stokes diameter of not more than a specified length, for example 2 μm, if 90% (by number) of those particles have a Stokes diameter of less than that specified length.

For the avoidance of doubt, particles of additive material are regarded as being within the scope of the invention if they have a diameter of not more than 2 μm according to any one of the definitions i) to iv) given above. Thus, particles of additive material are within the scope of the invention if they have a MMAD, a VED, a VMD or a Stokes diameter of less than 2 μm. The preferred measure is however MMAD and accordingly, preferably, the MMAD of theparticles of additive material is not more than 2 μm, advantageously not more than 1.5 μm, more advantageously not more than 1 μm and most advantageously not more than 0.8 μm.

The additive material is suitable for promoting the dispersal of particles of active substance upon actuation of a dry powder inhaler. Such additive materials, when included in a powder for use in a dry powder inhaler, increase the fine particle fraction of the active substance delivered upon actuation of the inhaler as compared to a similar powder not comprising the additive material (it is important not to add too much of some highly active additive materials to a composition comprising carrier particles as high levels of such additive materials can cause premature segregation of the active particles from the carrier particles as described in WO 96/23485). The fine particle fraction is a measure of the proportion of active substance leaving the inhaler which is in the form of particles having a size suitable for deposition in the lung. A procedure for measuring fine particle fraction using a multi stage impinger is given in the European Pharmacopoeia, Supplement 2000 at 2.9.18, Apparatus C (see pages 92 to 99).

The additive material comprises one or more of the following materials listed under 1) to 7):

1) Amino acids and derivatives thereof. Amino acids are physiologically acceptable and have been found to promote the release of the active particles on inhalation. Preferably, the amino acid or derivative thereof is crystalline (when included in the particles).

The additive material may comprise one or more of any of the following amino acids: leucine, isoleucine, lysine, valine, methionine, phenylalanine. The additive may be a salt or a derivative of an amino acid, for example aspartame or acesulfame K. Preferably, the additive particles consist substantially of an amino acid, more preferably of leucine, advantageously L-leucine. The D- and DL-forms may also be used. As indicated above, leucine has been found to give particularly efficient dispersal of the active particles on inhalation.

2) Phospholipids, for example a crystalline phospholipid, or a derivative thereof.
3) $C_{10}$ to $C_{22}$ carboxylic acids which may be linear or branched, saturated or unsaturated and derivatives (for example, esters, amides or salts) thereof, especially a metal stearate, for example, magnesium stearate.
4) Metal stearates, for example, magnesium stearate, calcium stearate, zinc stearate, sodium stearate or lithium stearate, or a derivative thereof, for example, sodium stearyl fumarate or sodium stearyl lactylate. Preferably, the additive material comprises magnesium stearate.
5) Solid state fatty acids such as oleic acid, lauric acid, palmitic acid, stearic acid, erucic acid, behenic acid, or derivatives (such as esters and salts) of those acids such as glyceryl behenate.
6) Phosphatadylethanolamines, phosphatidylcholines, phosphatidylglycerols, synthetic lung surfactants; and lecithins.
7) Sodium benzoate.

The additive material preferably comprises one or more materials selected from the group consisting of amino acids, crystalline phospholipids, glyceryl behenate, sodium stearyl fumarate and metal stearates (especially magnesium stearate.

The additive material is preferably also a hydrophobic additive material suitable for delaying the dissolution of an active substance in the lungs. The term "hydrophobic additive material suitable for delaying the dissolution of an active substance in the lungs" as used herein refers to an additive material which passes the test given below or which has a contact angle of greater than 90°. Preferably, the hydrophobic additive material has a contact angle of more than 90°, more preferably more than 95° and most preferably more than 100°. The skilled person will be aware of suitable methods of measuring the contact angle for a particular additive material.

Many of the additive materials described above which are suitable for promoting the dispersal of the active particles upon aerosolisation of a dry powder in a dry powder inhaler will also be suitable for delaying the dissolution of an active substance in the lung, especially if they are not soluble in water, for example, magnesium stearate, or have only a limited solubility in water.

The additive material may be a soft additive material. One measure of hardness is the indentation hardness (see Pharmaceutical Powder Compaction Technology, Ed. Goran Alderborn and Christer Nystrom, Marcel Dekker, Inc see especially pages 292 to 299—a particularly favoured method is that of Leuenberger mentioned therein). Soft additive materials are not easily milled using conventional milling methods to a particle size of below 4 μm. For the purposes of the invention, an additive material is regarded as "soft" when a sample cannot be milled to particles having a volume median diameter (as determined by light scattering) of less than 4 μm (see the test procedure below) or when the additive material has an indentation hardness of not more than about 100 MPa. The additive material may have an indentation hardness of not more than about 100 MPa, optionally not more than 50 MPa. Magnesium stearate is a soft additive material having an indentation hardness of 22 MPa. Because of the difficulties involved in conventional milling of soft additive materials, it will often be necessary to use alternative methods, for example homogenisation as described below, to provide particles of soft additive material of diameter 2 μm or less.

The particles of additive material may be in the form of individual particles or they may be in the form of agglomerates, each agglomerate consisting of a number of individual particles of the additive material. Such agglomerates will usually have a diameter greater than 2 μm, for example, a powder comprising particles of magnesium stearate according to the invention has appeared, when examined by electron microscopy, to comprise a large proportion of agglomerates having diameters up to 30 μm. However, upon closer examination, those agglomerates have been seen to be made up of individual particles of magnesium stearate having diameters less than 2 μm. The agglomerates are, however, loose agglomerates in the sense that they break up easily when mixed with particles of an active substance or upon dispersal from a dry powder inhaler.

Advantageously, the particles are of a size and shape such that they do not pack closely together and therefore have a low bulk density. Advantageously, the particles have a bulk density (as measured using the procedure below) of not more than 0.4 gcm$^{-3}$ advantageously not more than 0.2 gcm$^{-3}$, preferably not more than 0.1 gcm$^{-3}$. Advantageously, the particles are in the form of flakes having a thickness of not more than 0.5 μm. Preferably, the flakes have a thickness of not more than 100 nm. It is thought that particles in the form of such flakes may act as "spacers" between the particles of a powder, thereby improving the powder's flow properties. It is also thought that particles of additive material in the form of flakes may provide more effective coverage of the surface of active particles thereby (where the additive material is hydrophobic) more effectively reducing the rate of dissolution of the active substance.

The aspect ratio of a flake of additive material can be considered to be the (width of the particle)/(thickness of the particle). Advantageously, the number average aspect ratio of the particles is at least 2, preferably at least 5.

Observation of the thickness of the flakes may be made by studying electron microscope (SEM) images of the particles. For example, flakes may be mounted on an electron microscope stub with double sided tape and coated with gold prior to examination on an electron microscope.

Where reference is made above to the shape and size of the particles, it should be understood that the reference is to the shape and size of the individual particles. Those particles may become agglomerated to form clusters of individual particles as described above.

The invention also provides a composition for inhalation comprising particles of an active substance and particles of additive material as described above. The composition may include at least 0.01% by weight of the particles of additive material and preferably includes at least 1%, more preferably at least 2% by weight of those particles based on the weight of the composition. Preferably, the composition comprises not more than 60%, advantageously not more than 40% and optionally not more than 20% by weight of the particles of additive material.

Preferably, the composition is a dry powder and is suitable for use in a dry powder inhaler. Such compositions may consist essentially of only the active particles and additive particles or they may comprise additional ingredients such as carrier particles and flavouring agents. Carrier particles may be of any acceptable excipient material or combination of materials. For example, the carrier particles may consist substantially of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles are of a polyol. In particular the carrier particles may be particles consisting substantially of a crystalline sugar, for example mannitol, dextrose or lactose. Preferably, the carrier particles are of lactose.

Advantageously, substantially all (by weight) of the carrier particles have a diameter which lies between 20 μm and 100 μm, more preferably between 50 μm and 100 μm. Preferably, the diameter of substantially all (by weight) of the carrier particles is less than 355 μm and lies between 20 μm and 250 μm. Preferably at least 90% by weight of the carrier particles have a diameter between from 60 μm to 180 μm. The relatively large diameter (compared to the active substance) of the carrier particles improves the opportunity for other, smaller particles to become attached to the surfaces of the carrier particles and to provide good flow and entrainment characteristics.

The ratio in which the carrier particles (if present), active substance and particles of additive material are mixed will, of course, depend on the type of inhaler device used, the active substance used and the required dose. The carrier particles are preferably present in an amount of at least 50%, more preferably 70%, advantageously 90% and most preferably 95% based on the combined weight of the particles of active substance, particles of additive material and the carrier particles.

Where carrier particles are included in the pharmaceutical composition, that composition preferably also includes small particles comprised of the same or another excipient material as the carrier particles having, for example, a particle size between 5 to 20 μm. Preferably the small excipient particles are present in an amount of from 1% to 40%, more preferably 5% to 20% based on the weight of the carrier particles.

The terms "active particles" and "particles of active material" are used interchangeably herein. The active particles referred to throughout the specification will comprise one or more pharmacologically active substances. The active particles advantageously consist essentially of one or more pharmacologically active substances. Suitable pharmacologically active substances may be materials for therapeutic and/or prophylactic use. Active substances which may be included in the formulation include those products which are usually administered by inhalation for the treatment of disease such as respiratory disease, for example, β-agonists.

The active particles may comprise at least one $β_2$-agonist, for example one or more compounds selected from terbutaline, salbutamol, salmeterol and formeterol. If desired, the active particles may comprise more than one of those active substances, provided that they are compatible with one another under conditions of storage and use. Preferably, the active particles are particles of salbutamol sulphate. References herein to any active substance is to be understood to include any physiologically acceptable derivative. In the case of the $β_2$-agonists mentioned above, physiologically acceptable derivatives include especially salts, including sulphates.

The active particles may be particles of ipatropium bromide.

The active particles may include a steroid, which may be be clomethasone dipropionate or may be fluticasone. The active substance may include a cromone which may be sodium cromoglycate or nedocromil. The active substance may include a leukotriene receptor antagonist.

The active particles may include a carbohydrate, for example heparin.

The active particles may advantageously comprise a pharmacologically active agent for systemic use which is capable of being absorbed into the circulatory system via the lungs. For example, the active particles may comprise peptides or polypeptides such as Dnase, leukotrienes or insulin. Preferably, the active substance is a biological macromolecule, for example, a polypeptide, a protein, or a DNA fragment. The active substance may be selected from the group consisting of insulin, human growth hormone, cytokines, cyclosporin, interferons, gonadotrophin agonists and antagonists, erythropoietin, leptin, antibodies, vaccines, antisense ologonucleotides, calcitonin, somotastatin, parathyroid hormone, alpha-1-antitrypsin, Factor 7, Factor 8, Factor 9, and estradiol and pharmacologically active fragments and derivatives of those substances. Advantageously the active substance is selected from the group consisting of insulin, human growth hormone, cytokines, cyclosporin, interferons, gonadotrophin agonists and antagonists, erythropoietin, leptin, antibodies, vaccines and antisense oligonucleotides. The pharmaceutical compositions of the invention may in particular have application in the administration of insulin to diabetic patients, preferably avoiding the normally invasive administration techniques used for that agent. The active particles could also be used for the administration of other agents for example for pain relief (e.g. analgesics such as fentanyl or dihydroergotamine which is used for the treatment of migraine), anti cancer activity, anti-virals, antibiotics or the delivery of vaccines to the respiratory tract.

The pharmaceutical composition may comprise a propellant and be suitable for use in a pressurised metered dose inhaler.

The invention also provides a dry powder inhaler containing a dry powder composition as described above. In a further aspect the invention provides a pressurised metered dose inhaler which contains a composition comprising a propellant as described above.

The invention also provides a method for making particles of additive material for use in a composition for inhalation, the particles having a MMAD of not more than 2 μm, the method comprising the step of providing large particles of additive material having a MMAD of greater than 2 μm and the step of reducing the size of those particles such that the MMAD of the resulting particles is less than 2 μm. The step of reducing the size of the additive particles preferably involves breaking up the large particles of additive material.

The large particles of additive material may be of any size such that they have an MMAD of greater than 2 μm. Conveniently, the large particles of additive material will have diameters in the range 20 μm to 1000 μm, more conveniently in the range 50 to 250 μm.

The step of reducing the size of the large particles of additive material may involve milling. A wide range of milling devices and conditions are suitable for use in the method of the invention. Ball milling is a known method of size-reducing materials for use in pharmaceutical formulations but is not suitable for soft additive materials. The milling step may, alternatively, involve an agitator bead mill, for example, the DYNO-mill (Willy A. Bachofen AG, Switzerland). Other possible milling devices include air jet mills, pin mills, hammer mills, knife mills and ultracentrifugal mills.

The milling may be carried out in a closed vessel, for example in a ball mill. The use of a closed vessel prevents loss of ultrafine particles or vapour of the additive material which has been found to occur in jet milling or other open processes. Preferably, the milling is not jet milling.

Preferably, the milling is wet, that is, the milling step is carried out in the presence of a liquid. That liquid medium may be aqueous or non-aqueous, high or low volatility and of any solid content as long as it does not dissolve the additive particles to any significant degree and its viscosity is not so high that it prevents effective milling. The presence of a liquid medium helps to prevent compacting of the particles of additive material on the walls of the vessel. The method may then include a drying step for removing the liquid. The drying step may involve filtration followed by drying, or evaporation of the liquid. Preferably, the drying step is a spray drying step. Alternatively, the liquid may be evaporated slowly or the drying step may be a freeze drying step.

The milling may be dry, that is to say, there is no liquid present during the milling.

The milling may be more effective if carried out at a reduced temperature, for example, at a temperature of not higher than 0° C., preferable not higher than −50° C. and more preferably not higher than −100° C. For example, the milling may be carried out in the presence of solid carbon dioxide or liquid nitrogen.

Where, after the milling step, at least some of the particles of additive material are in the form of agglomerates and it is desired to break those agglomerates down or to reduce their size, the method may include a deagglomeration step. The deagglomeration step may involve mechanical breaking up of the unwanted agglomerates, for example, by forcing them through a sieve. The deagglomeration step may also be a spray drying step.

Conventional milling methods such as ball milling have, however, been found to be ineffective in reducing the MMAD of soft additive materials to the desired size. Preferably, the step of reducing the size of the particles of additive material involves the movement of a suspension of the particles in a liquid from a region of high pressure to a region of low pressure. Advantageously, the step of reducing the size of the particles of additive material involves homogenization, that is, the forcing of a suspension of the particles, in a liquid, through a constriction, for example, an orifice under pressure. For example, a high pressure homogenizer may be used in which a fluid containing the particles is forced through an orifice at high pressure producing conditions of high shear and turbulence. Shear forces on the particles, impacts between the particles and machine surfaces or other particles and cavitation due to acceleration of the fluid may all contribute to the fracture of the particles. Preferably, the step of reducing the size of the particles of additive material involves the use of shear forces in a liquid medium. Suitable homogenizers include EmulsiFlex® high pressure homogenizers which are capable of pressure up to 4000 Bar, Niro Soavi high pressure homogenizers (capable of pressures up to 2000 Bar), and Microfluidics Microfluidisers (maximum pressure 2750 Bar). Preferably, the homogenization is carried out at a pressure of at least 10,000 psi, preferably at least 20,000 psi. Preferably the homogenization is carried out for at least 60 minutes.

The liquid used in the homogenisation is preferably one in which the additive material is substantially insoluble. The homogenisation may, however, be carried out in a liquid in which the additive material is soluble to a limited extent so long as the amount of additive material that is present is such that not all of the additive material is dissolved.

Separation of the additive particles from the fluid may involve evaporation of the fluid, optionally followed by a drying stage, optionally followed by a brief milling step to break up any agglomerated mass or cake of particles.

Preferably, the step of reducing the size of the particles of additive material is conducted in the absence of the active substance.

The invention also provides a method of making a composition for inhalation which includes the step of mixing particles of additive material according to the invention with active particles. As mentioned directly above, that mixing may take place prior to or at the same time as the step of reducing the size of the additive particles. Otherwise, the mixing step may involve simple blending of the particles of additive material with the particles of active material. The mixing should evenly mix the particles.

Preferably, the method of making a composition for inhalation also comprises the step of pressing the particles of additive material together with the active particles. The particles of additive material are thereby applied to the surfaces of the active particles with more force than would be the case in a simple blending operation. One method of pressing the active and additive particles together is by ball milling a mixture of particles of additive material and active particles. As the mixture is repeatedly caught between the milling balls or between the milling balls and the wall of the chamber, those particles are pressed together. A preferred method is one where the mixture of particles is pressed against a surface, for example, as in a MECHANO-FUSION™ system (Hosokawa Micron Limited), or a CYCLOMIX™ (Hosokawa Micron Limited) in which a rotating member presses the particles against a surface, for example, the inner surface of a cylindrical chamber. A further preferred method is one in which the mixture is treated in a Hybridiser (Nara).

Especially preferred methods are those involving the MECHANO-FUSION™, Hybridiser and CYCLOMIX™ instruments.

Preferably, the milling step involves the compression of the mixture of active and additive particles in a gap (or nip) of fixed, predetermined width (for example, as in the MECHANO-FUSION™ and CYCLOMIX™ methods described below).

Some preferred milling methods will now be described in greater detail.

MECHANO-FUSION™

As the name suggests, this dry coating process is designed to mechanically fuse a first material onto a second material. The first material is generally smaller and/or softer than the second. The MECHANO-FUSION™ and CYCLOMIX™ working principles are distinct from alternative milling techniques in having a particular interaction between inner element and vessel wall, and are based on providing energy by a controlled and substantial compressive force.

The fine active particles and the additive particles are fed into the MECHANO-FUSION™ driven vessel, where they are subject to a centrifugal force and are pressed against the vessel inner wall. The powder is compressed between the fixed clearance of the drum wall and a curved inner element with high relative speed between drum and element. The inner wall and the curved element together form a gap or nip in which the particles are pressed together. As a result the particles experience very high shear forces and very strong compressive stresses as they are trapped between the inner drum wall and the inner element (which has a greater curvature than the inner drum wall). The particles violently collide against each other with enough energy to locally heat and soften, break, distort, flatten and wrap the additive particles around the core particle to form a coating. The energy is generally sufficient to break up agglomerates and some degree of size reduction of both components may occur. Embedding and fusion of additive particles onto the active particles may occur, and may be facilitated by the relative differences in hardness (and optionally size) of the two components. Either the outer vessel or the inner element may rotate to provide the relative movement. The gap between these surfaces is relatively small, and is typically less than 10 mm and is preferably less than 5 mm, more preferably less than 3 mm. This gap is fixed, and consequently leads to a better control of the compressive energy than is provided in some other forms of mill such as ball and media mills. Also, in general, no impaction of milling media surfaces is present so that wear and consequently contamination are minimised. The speed of rotation may be in the range of 200 to 10,000 rpm. A scraper may also be present to break up any caked material building up on the vessel surface. This is particularly advantageous when using fine cohesive starting materials.

The local temperature may be controlled by use of a heating/cooling jacked built into the drum vessel walls. The powder may be re-circulated through the vessel.

CYCLOMIX™ Method (Hosokawa Micron):

The CYCLOMIX™ comprises a stationary conical vessel with a fast rotating shaft with paddles which move close to the wall. Due to the high rotational speed of the paddles, the powder is propelled towards the wall, and as a result the mixture experiences very high shear forces and compressive stresses between wall and paddle. Such effects are similar to the MECHANO-FUSION™ as described above and may be sufficient to locally heat and soften, to break, distort, flatten and wrap the additive particles around the active particles to form a coating. The energy is sufficient to break up agglomerates and some degree of size reduction of both components may also occur depending on the conditions and upon the size and nature of the particles.

Hybridiser Method:

This is a dry process which can be described as a product embedding or filming of one powder onto another. The fine active particles and fine or ultra fine additive particles are fed into a conventional high shear mixer premix system to form an ordered mixture. This powder is then fed into the Hybridiser. The powder is subjected to ultra-high speed impact, compression and shear as it is impacted by blades on a high speed rotor inside a stator vessel, and is re-circulated within the vessel. The active and additive particles collide with each other. Typical speeds of rotation are in the range of 5,000 to 20,000 rpm. The relatively soft fine additive particles experience sufficient impact force to soften, break, distort, flatten and wrap around the active particle to form a coating. There may also be some degree of embedding into the surface of the active particles.

Where the composition is a powder for use in a dry powder inhaler, the method may also include the addition of other components such as carrier particles and flavouring agents. Again, the mixing should be sufficient to evenly distribute the various components throughout the powder. Preferably, the active particles and the particles of additive material are mixed together before the addition of any further components.

Where the composition is for use in a pressurised metered dose inhaler, the particles of additive material and the particles of active material are preferably mixed as described above prior to addition of the propellant. For example, the active particles and the particles of additive material may be mixed and then a weighed amount of the mixture may be charged to a bottle or canister. The bottle or canister is then fitted with an actuator through which the propellant is added.

The invention also provides the use of particles of additive material according to the invention in a composition for inhalation comprising active particles to promote the dispersal of active particles upon actuation of an inhaler.

The invention also provides the use of particles of additive material according to the invention, in a composition for inhalation comprising active particles, for delaying the dissolution of the active particles in the lung.

In a further aspect, the invention provides a method of therapy comprising the step of administering a composition for inhalation according to the invention to a human being or an animal in need thereof.

The present invention also provides particles of an additive material for use in a composition for inhalation, the particles having a diameter (as described below) of not more than 21 µm.

Examples of the invention will now be described for the purposes of illustration only with reference to the Figures in which.

TEST PROCEDURES

1) Standard Formulation for a Dissolution Test

In order to determine whether or not a particular additive material is a hydrophobic additive material suitable for delaying the dissolution of the active substance in the lung, the following test is carried out.

A standard test formulation is prepared in the following manner:

A mixture of micronised salbutamol sulphate (active substance) and the additive material to be tested in the ratio of 75:25 by mass (total mass of approximately 1 g) is placed in a ball mill chamber on top of 100 g of 2 mm diameter stainless steel balls. The mill chamber volume is approximately 58.8 $cm^3$. 5 $cm^3$ of an inert liquid, which is a non-solvent for the additive material to be tested and for the salbutamol sulphate, is added to wet the mixture. The mill is sealed and secured in a Retsch S100 centrifuge. Centrifugation is then carried out at 500 rpm for 240 minutes in total. A small sample (approximately 5-10 mg) of wet powder is removed from the mill after 60 minutes. The sample is then dried in an oven at 37° C. under vacuum for 2 hours or as long as necessary to remove the inert non-solvent. The following dissolution test is then carried out.

The dry powder is tested using an apparatus comprising a 195 $cm^3$ reservoir filled with deionised water and having an inlet port and an outlet port. A sintered glass disc of approximately 50 mm diameter and 3 mm depth occupies an opening at the top of the reservoir and sits horizontally in contact with the water. The water in the reservoir is stirred by a stirrer.

A known mass of approximately 1 mg of the formulation to be tested is placed on the sinter and a timer is started. At various times, 1 $cm^3$ samples of the water are removed from the reservoir and are immediately replaced with 1 $cm^3$ deionised water to maintain the volume in the reservoir. The concentration of the active substance in the 1 $cm^3$ samples is determined by a suitable method, for example, HPLC. The particular method will, of course, depend on the nature of the active substance but such methods will be known to the skilled person.

A graph of concentration of the active substance in the reservoir of water versus time is then plotted.

The procedure is repeated using 0.75 g of the active substance in the absence of the additive material in order to provide a basis for comparison.

If the graph of concentration versus time for the salbutamol sulphate combined with the additive material shows that the salbutamol sulphate in that combination has dissolved more slowly than the salbutamol sulphate alone (in the sense that it has taken longer to reach its maximum concentration), the hydrophobic material is regarded as being suitable for delaying the dissolution of the active substance.

The degree to which the additive material delays the dissolution of the active substance is a measure of the efficiency of the additive material. In particular, where it is desired to measure the delayed release performance of a particular formulation, that can be done by carrying out the standard dissolution test given above on a sample of the formulation to be tested and upon a (control) sample of the active substance. For a true comparison the particle size distribution of the particles of the active substance must be the same or similar in the sample of formulation to be tested as in the (control) sample of active substance. The rate of dissolution of the active substance in the formulation to be tested as a percentage of the rate of dissolution of the active substance alone can then be calculated.

Thus, for example, if the concentration of the active substance in the dissolution test on the formulation reached a maximum at 40 minutes and the concentration of the active substance alone reached a maximum at 10 minutes, the % rate of dissolution for the formulation would be $10/40\times100=25\%$, corresponding to a decrease in the rate of dissolution of 75%.

An alternative method of determining whether or not a particular additive material is a hydrophobic additive material suitable for delaying the dissolution of the active substance in the lung is to measure the contact angle. Additive materials having contact angles greater than 100° are also regarded as hydrophobic additive materials.

2) Milling Test for "Soft Materials"

Approximately 1 g of particles of the additive material to be tested having a volume median diameter of at least 50 μm is placed in a ball mill chamber on top of 100 g of 2 mm diameter stainless steel balls. The mill chamber volume is approximately 58.8 $cm^3$. The mill is sealed and secured in a Retsch S100 centrifuge. Centrifugation is then carried out at 500 rpm for 240 minutes at 25° C. in total. A small sample (approximately 5-10 mg) of powder is removed from the mill after 60 minutes.

The particle size distribution of the powder is then measured by laser light scattering. If the volume median diameter is not less than 4 μm then the additive material is regarded as soft.

An alternative measure of softness is the indentation hardness. An additive material is regarded as soft if it has an indentation hardness of not more than 100 MPa.

EXAMPLE 1

Homogenised Magnesium Stearate 240 g magnesium stearate (Riedel de Haen, particle size by Malvern laser diffraction: $d_{50}$=9.7 μm) was suspended in 2150 g dichloroethane. That suspension was then mixed for 5 minutes in a Silverson high shear mixer. The suspension was then processed in an Emulsiflex® C50 high pressure homogenizer fitted with a heat exchanger at 1000 psi for 20 minutes in circulation mode (300 $cm^3$/min) for 20 minutes. The suspension was then circulated at atmospheric pressure for 20 minutes to allow it to cool. The next day, the suspension was processed in circulation mode (260 $cm^3$/min) at 20000 psi for 30 minutes. The dichloroethane was removed by rotary evaporation followed by drying in a vacuum oven at 37° C. overnight. The resulting cake of material was broken up by ball milling for 1 minute.

FIG. 1 shows the magnesium stearate before the processing. That magnesium stearate largely consists of particles of diameter greater than 5 μm. FIG. 2 shows the magnesium stearate after the homogenisation. That magnesium stearate is in the form of particles which appear to have diameters in the range of 0.25 to 2 μm and which are grouped together to form an agglomerate.

The volume median diameter d50, as determined on a Malvern laser light scattering instrument, of the homogenized magnesium stearate particles according to the invention was approximately 2.5 μm due to the presence of agglomerates and, for the avoidance of doubt, those agglomerates are within the scope of the invention because they consist of particles according to the invention. A sample of the magnesium stearate was subjected to ultrasound treatment to reduce the degree of agglomeration and the light scattering measurement was repeated after 15, 30, 45 and 60 minutes ultrasound treatment. The results are given in Table 1.

TABLE 1

Light scattering results with ultrasound treatment

| Sonication time/min | d50/μm |
|---|---|
| 15 | 2.5 |
| 30 | 2.1 |
| 45 | 1.9 |
| 60 | 1.7 |

As can be seen from the table, as the number and size of the agglomerates is reduced by the ultrasound treatment, the measured d50 reduces.

EXAMPLE 2

Salbutamol Sulphate/Magnesium Stearate Blends

Figure 1:
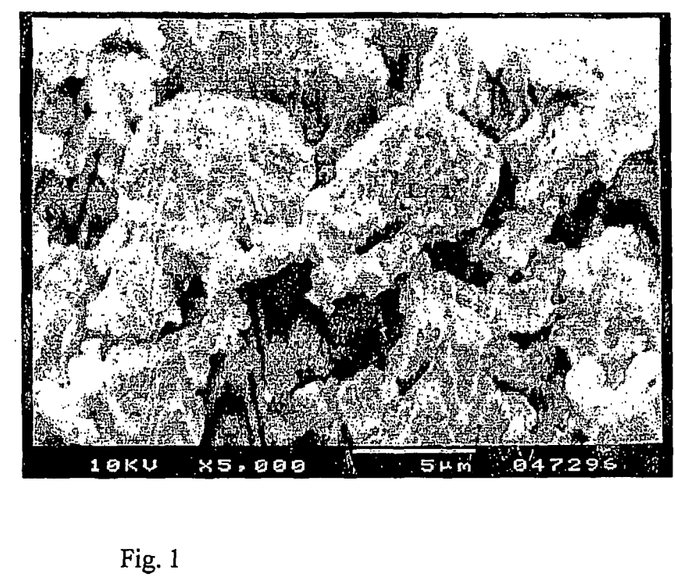
FIG. 1 is an electron micrograph of unprocessed magnesium stearate.
Figure 2:
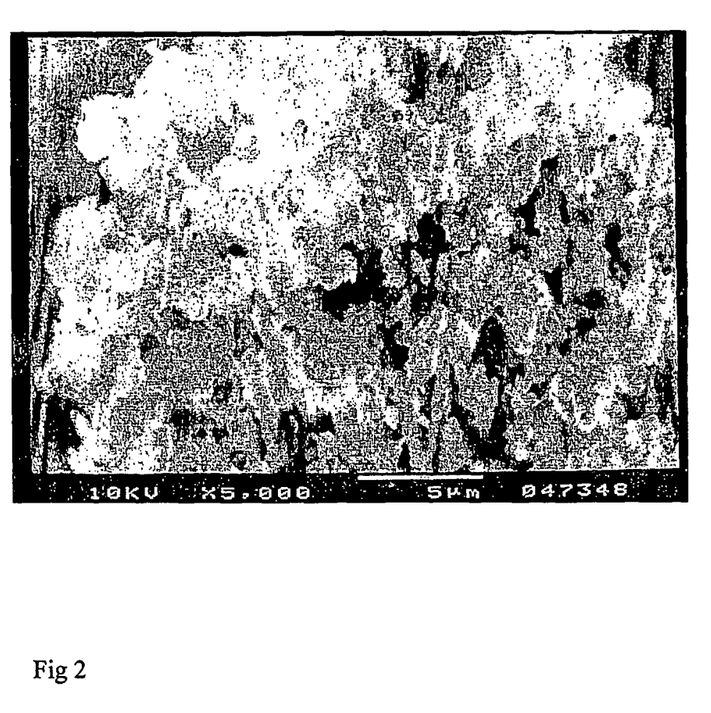
FIG. 2 is an electron micrograph of magnesium stearate particles according to the invention.
Figure 3:
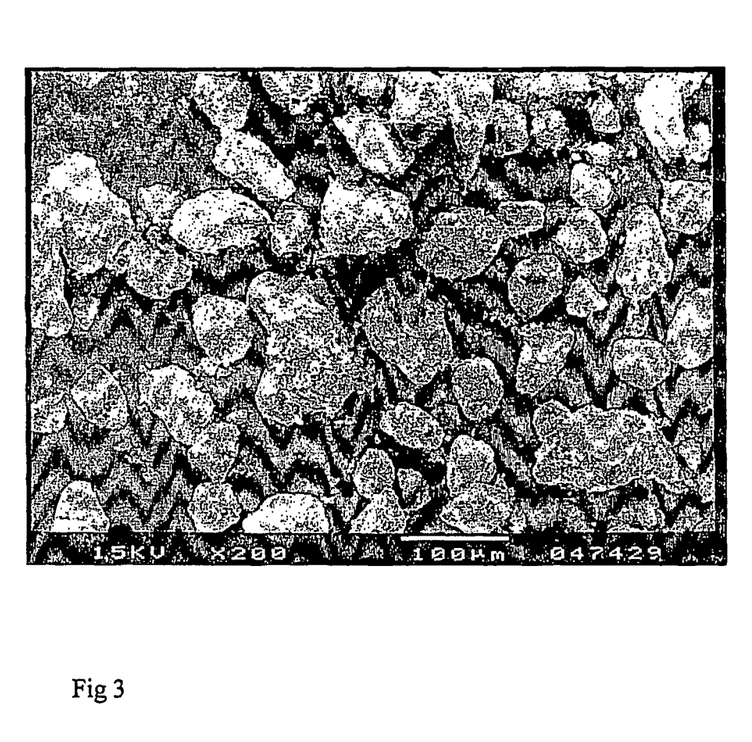
FIG. 3 is an electron micrograph of a 9:1 blend of salbutamol sulphate and the magnesium stearate shown in FIG. 2.

A 9:1 by weight blend of salbutamol sulphate and the homogenized magnesium stearate obtained from the above process was prepared by blending the two materials with a spatula. FIG. 3 shows an electron micrograph of the blended material from which it is clear that the blend was mostly in the form of agglomerated particles, the agglomerates having diameters of 50 μm and above. The blend was then processed in a MECHANO-FUSION™ mill (Hosokawa) as follows:

Machine data: Hosokawa MECHANO-FUSION™: AMS-Mini Drive: 2.2 kw Housing: stainless steel Rotor: stainless steel Scraper: None Cooling: Water Gas purge: None All samples were premixed for 5 minutes by running the machine at 1000 rpm. The machine speed was then increased to 5050 rpm for 30 minutes. The procedure was repeated for salbutamol sulphate/magnesium stearate in the following weight ratios: 19:1, 3:1, 1:1.

Figure 4:
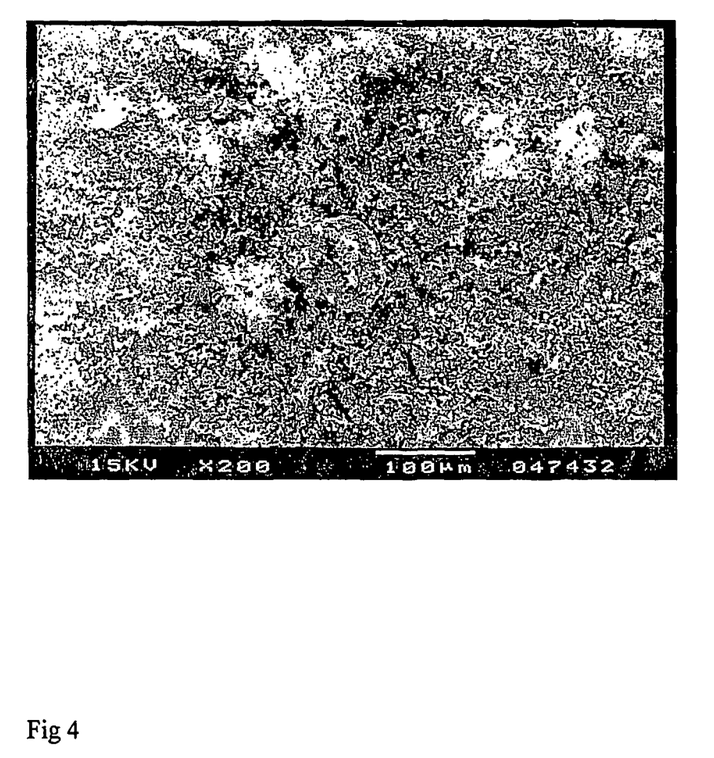
FIG. 4 is an electron micrograph of the blend of FIG. 3 after Mechano-Fusion treatment.

An electronmicrograph of the processed 9:1 material is shown in FIG. 4. That Figure indicates that the material is mostly in the form of simple small particles of diameter less than 5 μm or in very loose agglomerates of such particles with only one agglomerate of the original type being visible.

The 3:1 and the 19:1 blends were then each loaded into a 20 mg capsule and fired into a twin stage impinger. A sample of unprocessed salbutamol sulphate was also fired from the TSI to provide a comparison The fine particle fractions were then calculated and are given in Table 2.

TABLE 2

Fine Particle Fraction results for salbutamol sulphate blends.

| Composition | Fine Particle Fraction % |
|---|---|
| Salbutamol sulphate | 28 |
| salbutamol sulphate/magnesium stearate 19:1 | 66 |
| salbutamol sulphate/magnesium stearate 3:1 | 66 |

1 g sample of the 3:1 blend was suspended by ball milling in 10 cm³ dichloromethane for 5 minutes. The suspension was then spray dried on a Buchi B191 spray dryer using the following conditions inlet T=50° C., aspirator 100%, liquid flow 10 cm³/min nozzle air flow 800 dm³/hr.

Figure 5:
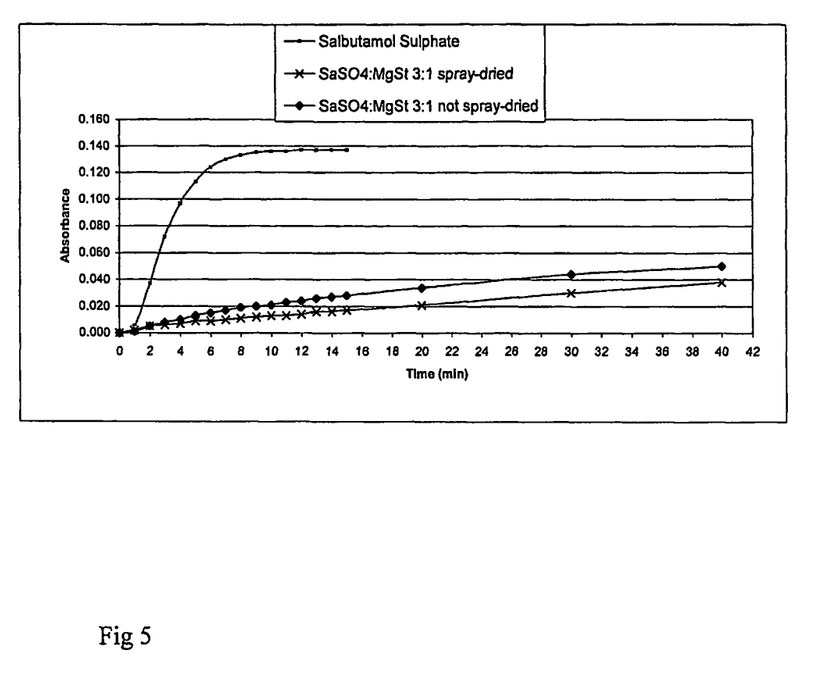
FIG. 5 shows dissolution curves for salbutamol sulphate and salbutamol sulphate/magnesium stearate blends.

The 3:1 blend, the spray dried 3:1 blend and a sample of salbutamol sulphate were then each tested for dissolution rate using the procedure outlined above. The results are shown in FIG. 5. It is clear from FIG. 5 that the 3:1 blend of salbutamol sulphate:magnesium stearate dissolves at a significantly slower rate than the salbutamol sulphate with no magnesium stearate. That delayed dissolution effect is shown by the spray dried sample of the 3:1 blend. That contrasts to the results of similar experiments carried out using blends of drug and magnesium stearate where the magnesium stearate has not been homogenized (and does not have a particle size below 2 μm) in which spray drying of the blend has produced a significant reduction of the delayed dissolution effect.

Figure 6:
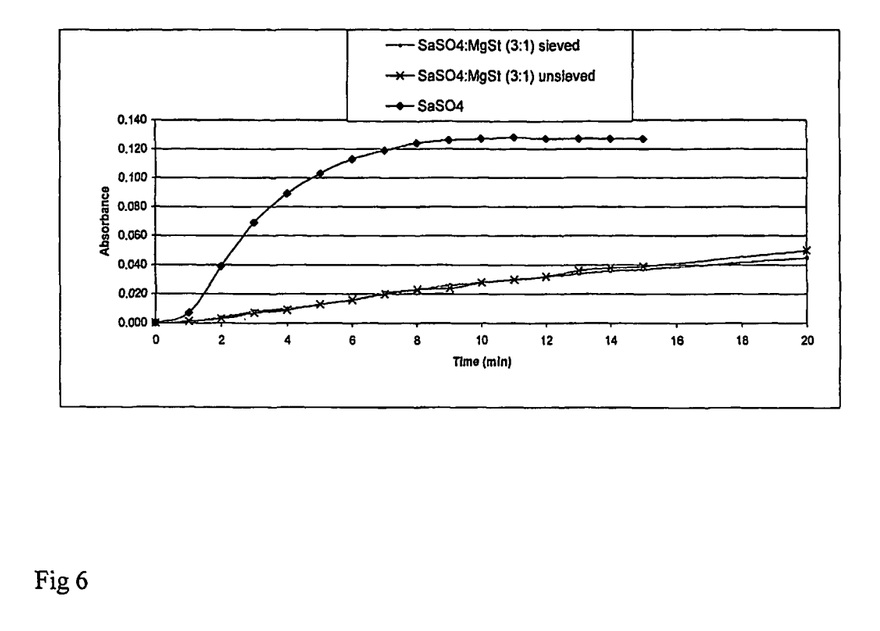
FIG. 6 shows dissolution curves for sieved and unsieved blends of salbutamol sulphate and magnesium stearate.

To test the effect of any agglomeration in the blend upon the dissolution rate of the salbutamol sulphate in the blends a sample of the 3:1 salbutamol sulphate:magnesium stearate blend was brushed through a 45 μm sieve. FIG. 6 shows the dissolution curves for the sieved and unsieved blends and for salbutamol sulphate. It can be seen that the sieved and unsieved 3:1 blends had the same dissolution rate.

The invention claimed is:

1. A method of making a composition for inhalation comprising
    reducing in size particles of additive material to produce particles with an MMAD of not more than 2 μm;
    and mixing the additive particles with active particles, wherein the additive material is suitable for promoting dispersal of active particles upon aerosolisation of a dry powder in a dry powder inhaler;
    wherein said additive material is soft, having an indentation hardness of not more than 100 MPa;
    and wherein the step of reducing in size particles of additive material is performed dry;
    wherein the method further comprises the step of fusing the particles of additive material to the surfaces of the active particles by compressing the mixture of active and additive particles using a milling process selected from ball milling, mechano-fusion, a cyclomix method, a hybridiser method, agitator bead milling, jet milling, pin milling, hammer milling, knife milling, and ultracentrifugal milling.

2. A method as claimed in claim 1, in which the additive particles have a diameter of not more than 1.5 μm.

3. A method as claimed in claim 1, wherein the additive material is also a hydrophobic material suitable for delaying dissolution of an active substance in a lung.

4. A method as claimed in claim 1, wherein the additive material comprises magnesium stearate.

5. A method as claimed in claim 1, in which the additive material comprises a phospholipid.

6. A method as claimed in claim 5, wherein said additive material is lecithin.

7. A method as claimed in claim 1 in which the additive particles are agglomerated.

8. A method as claimed in claim 1 in which the additive particles have a bulk density not more than 0.4 gcm$^{-3}$.

9. A method as claimed in claim 1 in which the additive particles are in a form of flakes having a thickness of not more than 0.5 µm.

10. A method as claimed in claim 1 further comprising a step of providing large particles of additive material having a MMAD of greater than 2 µm and the step of reducing the size of those particles such that the MMAD of the resulting particles is less than 2 µm.

11. A method as claimed in claim 10 in which the particles of active material are also present during the step of reducing the size of the particles of additive material.

12. A composition for inhalation comprising particles of an active substance and additive particles, the composition prepared by a method as claimed in claim 1, wherein the particles have aerodynamic diameters in the range of 2 to 0.05 µm.

13. A composition as claimed in claim 12, which is a powder and is suitable for use in a dry powder inhaler.

14. A composition as claimed in claim 12 further comprising a propellant and is suitable for use in a pressurized metered dose inhaler.

15. A dry powder inhaler comprising a composition as claimed in claim 13.

16. A pressurized metered dose inhaler which comprises a composition as claimed in claim 14.

17. A method of promoting the dispersal of active particles of a composition for inhalation upon aerosolisation of an inhaler, the method comprising reducing in size particles of additive material to produce particles with an MMAD of not more than 2 µm;

mixing the additive particles with active particles;

and fusing the particles of additive material to the surfaces of the active particles, by compressing the mixture of active and additive particles using a milling process selected from ball milling, mechano-fusion, a cyclomix method, a hybridiser method, agitator bead milling, jet milling, pin milling, hammer milling, knife milling, and ultracentrifugal milling;

wherein said additive material is soft, having an indentation hardness of not more than 100 MPa, wherein the step of reducing in size of particles of additive material is performed dry.

18. A method of delaying dissolution of active particles of a composition for inhalation; the method comprising reducing in size particles of additive material to produce particles with an MMAD of not more than 2 µm;

mixing the additive particles with active particles;

and fusing the particles of additive material to the surfaces of the active particles, by compressing the mixture of active and additive particles using a milling process selected from ball milling, mechano-fusion, a cyclomix method, a hybridiser method, agitator bead milling, jet milling, pin milling, hammer milling, knife milling, and ultracentrifugal milling;

wherein the additive material is soft, having an indentation hardness of not more than 100 MPa, wherein the step of reducing in size particles of additive material is performed dry, said delayed dissolution is as compared to the dissolution of the active particles in the absence of the additive material.

19. A method of therapy comprising a step of administering a composition for inhalation as claimed in claim 12 to a human being or animal in need thereof.

* * * * *

UNITED STATES PATENT AND TRADEMARK OFFICE
CERTIFICATE OF CORRECTION

PATENT NO.           : 8,580,306 B2                                    Page 1 of 1
APPLICATION NO.  : 10/433135
DATED                   : November 12, 2013
INVENTOR(S)         : Staniforth et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 210 days.

Signed and Sealed this
Twenty-second Day of September, 2015

Michelle K. Lee
*Director of the United States Patent and Trademark Office*